(12) United States Patent
Pringle

(10) Patent No.: US 7,243,526 B2
(45) Date of Patent: Jul. 17, 2007

(54) DEVICE AND METHOD FOR MEASURING THE IMPACT PROPERTIES OF A SPORT FIELD SURFACE

(75) Inventor: Matthew M. Pringle, Bordentown, NJ (US)

(73) Assignee: United States Golf Association, Far Hills, NJ (US)

( * ) Notice: Subject to any disclaimer, the term of this patent is extended or adjusted under 35 U.S.C. 154(b) by 0 days.

(21) Appl. No.: 11/060,107

(22) Filed: Feb. 16, 2005

(65) Prior Publication Data

US 2006/0179917 A1 Aug. 17, 2006

(51) Int. Cl.
*G01M 13/00* (2006.01)
*G01M 7/00* (2006.01)

(52) U.S. Cl. .................................................. 73/12.09

(58) Field of Classification Search .... 73/12.01–12.14, 73/78–85
See application file for complete search history.

(56) References Cited

U.S. PATENT DOCUMENTS 3,731,538 A * 5/1973 Jacoby ..................... 73/382 R
3,946,598 A * 3/1976 Towne et al. ................. 73/594
5,490,411 A * 2/1996 Hogan ......................... 73/12.13
5,537,862 A * 7/1996 Scarton et al. ................. 73/82
5,736,631 A * 4/1998 Dixon et al. ............... 73/12.06
5,769,370 A * 6/1998 Ashjaee ..................... 248/181.1
7,040,146 B2 * 5/2006 Mackenzie et al. ............. 73/81
2004/0182131 A1* 9/2004 Pringle et al. ............. 73/12.09
2005/0076709 A1* 4/2005 Mackenzie et al. ............. 73/81

OTHER PUBLICATIONS

Indiveri et al., System Implementations of Analog VLSI Velocity Sensors, Oct. 1996, IEEE Micro, pares 40-49 ; ieeexplore.ieee.org/iel1/40/11599/00540079.pdf?tp=&arnumber=540079 &isnumber=11599.*

* cited by examiner

*Primary Examiner*—Max Noori
(74) *Attorney, Agent, or Firm*—Francis C. Hand; Carella, Byrne, Bain, et al.

(57) ABSTRACT

The tuft impact tester mounts a test probe in a suspended manner from a tripod arrangement via a gimbals mechanism so that the test probe is able to move along a vertical axis. The test probe is dropped from a predetermined height, the velocity of the test probe is measured prior to impact on a ground surface and the deceleration of the test probe caused by the ground surface is measured. The two values are used to determine the relative hardness of the ground surface.

15 Claims, 3 Drawing Sheets

FIG. 1
FIG. 2
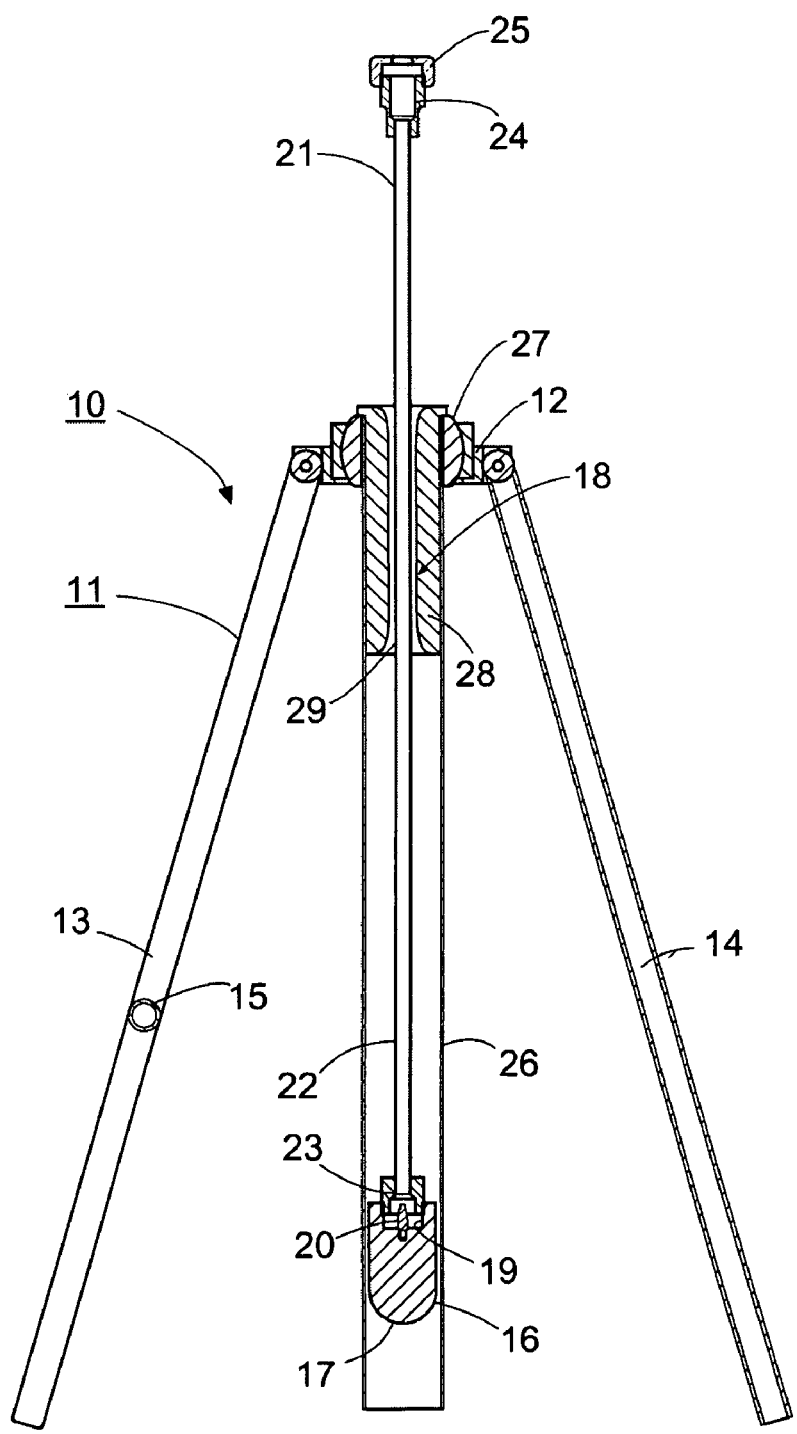
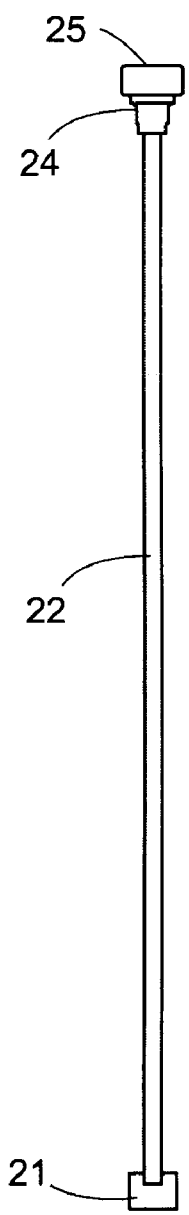

DEVICE AND METHOD FOR MEASURING THE IMPACT PROPERTIES OF A SPORT FIELD SURFACE

This invention relates to a device and method for measuring the impact properties of a sports field surface. More particularly, this invention relates to a device and method for measuring the impact properties of the surfaces of a golf course, baseball field, football field, tennis court, cricket field and the like.

As is known, the condition of the surface of a sports field will have an effect on a ball that impacts the surface of the field, for example, the surface of a golf course will have an effect on a golf ball that impacts against the surface of a course. For example, if the ground surface is hard, a golf ball will bounce after impact and may continue to do so depending on the hardness of the course. On the other hand, if the surface is wet and spongy, a golf ball may "plug" in the ground and not bounce at all.

Typically, golf greens are maintained in a manner to be consistent from day to day, particularly during multi-day tournaments. Should a golf green become dried out due to weather conditions and become harder than normal, a golf ball landing on the green will bounce more than normal. Likewise, if the golf green has become softer than normal, for example due to a rainstorm, a golf ball landing on the green may plug. Consequently, knowledge of the conditions of the greens is important for a grounds-keeper in order to have the greens maintain consistency during a multi-day tournament.

It has also been known that there are various types of instruments available for assessing the impact characteristics of a ground surface. For example, use has been made of a Clegg Impact Soil Tester to determine the impact characteristics of a soil, for example, for road building purposes, and for measuring the hardness of athletic fields. Basically, the Clegg Impact Soil Tester is used to obtain a measurement of the deceleration of a free falling mass (hammer) from a set height onto a surface under the device. The impact of the hammer produces an electrical pulse which is to be converted into a Clegg Impact Value that is then correlated to the California Bearing Ratio or other such standards. The obtained values are in units of gravity, such as 93 gmax, to provide an indication of the load capabilities of the soil.

Other instruments, such as soil penetrometers, have also been used for measuring the resistance, or amount of pressure, required to push a tipped rod through a soil. In such cases, the rod tip is equipped with a load-sensing cell to record the soil strength as the strength varies throughout the soil depth. However, such soil penetrometers are extremely complex and require some practice to use correctly and are expensive. Furthermore, the load type of the penetrometer is significantly different from that of a sphere impacting a sports field surface which can lead to significant errors in characterizing this surface.

Accordingly, it is an object of the invention to provide a technique for determining the relative impact properties of a sports field surface in a simple reliable manner.

It is another object of the invention to provide a relatively simple structure for measuring the impact properties of a sports field surface.

It is another object of the invention to be able to determine the relative hardness of a golf green.

It is another object of the invention to provide an inexpensive instrument for determining a deviation of the hardness of a golf green from a standard value.

It is another object of the invention to provide an instrument that can be used by grounds-keepers to maintain a level of consistency in the hardness characteristics of the golf greens of a golf course.

It is another object of this invention to use both the reversible and permanent deformation relationships between force and displacement to fully describe the material response of a sports field surface.

Briefly, the invention provides an instrument to repeatedly impact the surface of a sports field in order that the response of the surface to impact may be characterized.

In accordance with the invention, a test probe of specified mass and shape is released from a prescribed height and the impact of the test probe on the sports field surface is recorded along with a measurement of the pre-impact velocity of the test probe. This information, combined with various models of the response of a sports field surface, permits the user to quantify several key parameters of the sports field surface. These parameters include, but are not limited to, stiffness in loading, stiffness in unloading and collision energy absorption. Furthermore, the use of the data, combined with the appropriate impact models, permits the user to estimate the rebound spin, angle and spin of a sports ball prior to impact.

In one embodiment, the instrument is constructed as a turf impact tester that uses a test probe with a part spherical impact surface, means for supporting the test probe for movement under gravity along a vertical axis from a predetermined position to a position of impact with a ground surface and an accelerometer for determining the deceleration of the test probe during impact with the ground surface and for emitting a corresponding signal in response.

In addition, an oscilloscope or other recording device is operatively connected to the accelerometer to receive the signal and record the acceleration of the impact, i.e. the deceleration of the test probe.

The turf impact tester may also include a speed sensing means for sensing the speed of the test probe prior to impact with the ground surface in order to increase accuracy.

The surface of the test probe presents a spherical face having a radius equal to that of a golf ball. The mass of the probe, in conjunction with the impact velocity is specified such that the energy of the impact is similar to that of an inbound golf ball with the target surface. For sports other than golf, the radius of the face of the probe and the impact energy should be altered to be consistent with the sport of interest.

The test probe is attached to a handle of specified length. The length of the handle is prescribed such that impact velocity is in the desired range to provide appropriate impact energy. The handle rides in a linear bearing that permits low friction linear motion of the handle. The linear bearing is seated in a guide tube, The purpose of the guide tube is to protect the probe and handle from debris and damage. The guide tube may be connected at top to a gimbals mechanism in order to improve the repeatability of the pre-impact velocity. The gimbals mechanism permits the guide tube to hang plumb under the influence of gravity such that the release of the probe and handle are perfectly vertical.

Finally, the gimbals mechanism is attached to a tripod or other pedestal that supports the gimbals/guide tube assembly and permits the assembly to hang freely in a depending manner along a vertical axis.

The mechanical improvements of the instrument permit a repeatable release and pre-impact velocity.

The use of a speed sensing system to measure the speed of the probe immediately prior to impact may be used to increase the accuracy of the instrument. Such a system may employ any one of a number of measurement strategies, such as (i) a high sensitivity accelerometer to measure the acceleration of the probe during descent, (ii) the probe may be equipped with magnets and a coil wrapped around the guide tube such that the voltage generated in the coil is proportional with the velocity of the probe, or (iii) the probe may be equipped with magnets and a series of Hall effect sensors may be affixed to the guide tube such that the velocity of the probe may be calculated from the time delay between triggering of the Hall effect sensors. Most preferably, however, a regular series of light and dark bands are produced on the outer circumference of the probe and an integrated light source/light sensor is attached to the guide tube. As the light and dark bands pass in front of the light source/light sensor, the output of the sensor will change as a result of the reflectivity of the bands. The velocity of the probe then can be calculated by measuring the rate of change of the output of the sensor as the light and dark bands pass the light source/light sensor.

In addition to the mechanical components and the speed sensing system, a computer is used to analyze and log the data gathered by the speed sensing system as well as providing the user outputs of the sports field parameters.

In use, the user sets the turf impact tester over the area of interest. The guide tube will, via the gimbals mechanism, hang vertically. The operator activates the software and then raises the probe via the handle until the predetermined release height has been reached. This release height is calculated (in conjunction with the mass of the probe) to deliver impact energy that is consistent with the impact of a ball of interest with the sports field.

The operator then releases the handle such that, under the influence of gravity, the test probe falls while accelerating and strikes the ground. If the instrument is equipped with a speed sensor, the speed of the probe is measured immediately prior to impact. Upon impact, the sports field decelerates the probe and the oscilloscope via the accelerometer affixed to the probe records this deceleration.

The user may then move the entire unit to sample other areas of interest and repeat the procedure such that the characteristics of individual areas or composite or average characteristics for a broader area may be calculated.

The impact with the sports field surface will fall into two categories. The most common is the impact with granular materials, such as soils, sands or other compacted granular surfaces of man-made materials. The other sports surfaces are constructed from man-made materials, such as foam gymnasium surfaces, artificial turf and the like. While there are significant differences in the materials and construction of these two forms of sports field surfaces, their response appears to share similar features such that a uniform approach to characterizing that response may be made.

The speed sensing system provides an output of the pre-impact velocity of the test probe and the acceleration time history during the impact with the sports field surface. Knowing the mass of the probe permits the force between the probe and the sports field surface to be calculated and to be used to obtain the characteristic of the area being monitored.

These and other objects and advantages of the invention will become more apparent from the following detailed description taken in conjunction with the accompanying drawings wherein:

FIG. 1 illustrates a part cross-sectional view of a turf impact tester constructed in accordance with the invention;

FIG. 2 illustrates a probe and handle assembly in accordance with the invention;

Figure 4:
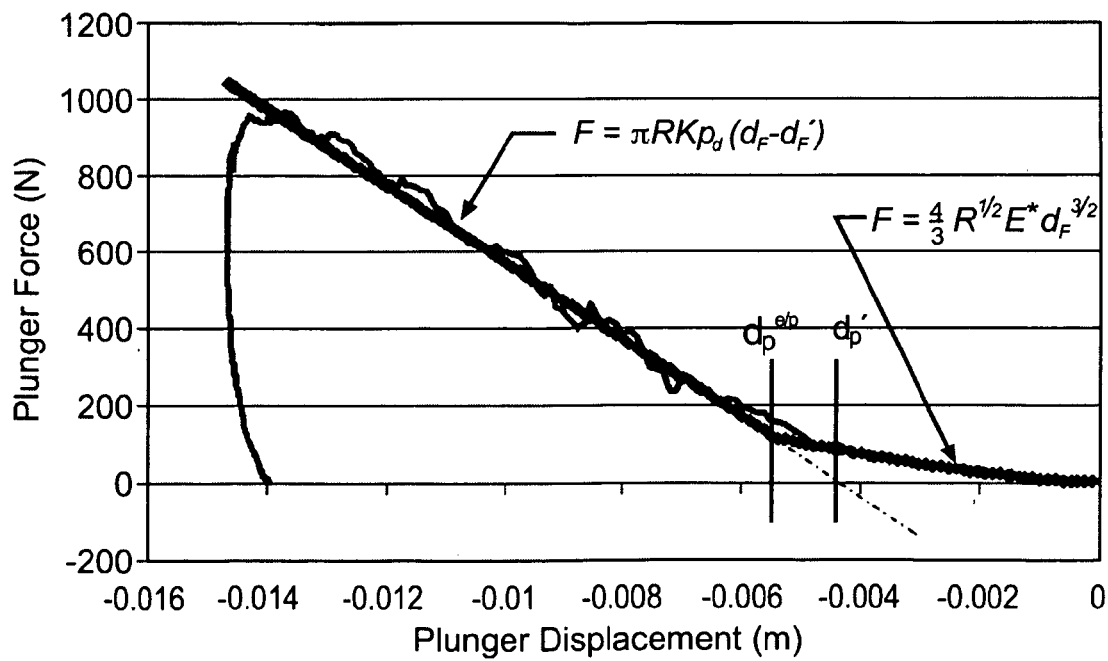
Figure 5A:
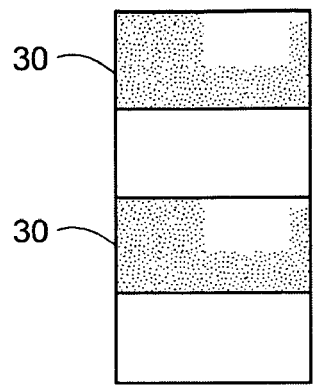
Figure 5B:
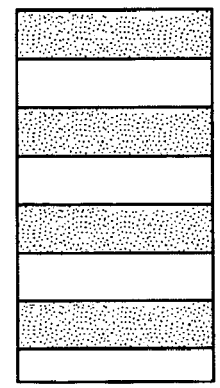
Figure 5C:
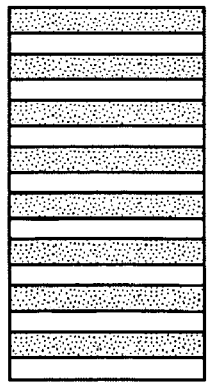
Figure 5D:
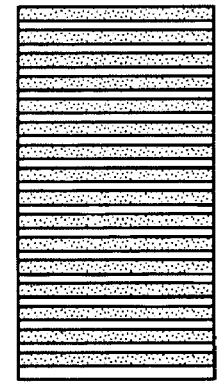
Figure 5E:
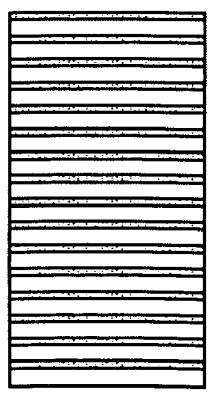
Figure 5F:
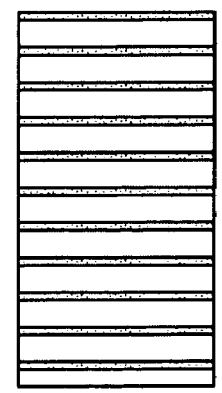

FIG. 4 graphically illustrates a force-displacement relationship with resultant material properties in accordance with the invention; and FIG. 5 illustrates several patterns of light and dark bands that may be used on the test probe for sensing the falling velocity of the test probe in use.

Referring to FIG. 1, the turf impact tester 10 has a support, for example, in the form of a tripod arrangement 11 having a support plate 12 of annular construction, a double leg frame 13 pivotally mounted on one side of the plate and a single leg frame 14 pivotally mounted on a diametrically opposite side of the plate 12. Both leg frames 13, 14 are hingedly connected to the plate 13 so as to be collapsed for ease of transport. The double leg frame 13 has a pair of legs (only one of which is illustrated) that are interconnected by a horizontal strut 15.

Referring to FIGS. 1 and 2, the turf impact tester 10 also has a test probe 16 with a part-spherical impact surface 17 and a means 18 for supporting the test probe 16 in the tripod arrangement 11 for movement under gravity along a vertical axis from a predetermined position to a position of impact with a ground surface.

Referring to FIG. 1, the test probe 16 is of ballistic shape and has a recess 19 in an end opposite the part spherical impact surface 17. In addition, a counterbore is provided within the recess 19 in order to receive an accelerometer 20 for purposes as described below.

The means 18 for supporting the test probe 16 in the tripod arrangement 11 includes a handle assembly 21 having an elongated handle 22 in the form of a hollow shaft and an externally threaded adapter 23 that is fixed to the lower end of the handle 22. The shaft 22 is hollow to allow a wire from the accelerometer 20 to run up to the top of the shaft 22.

The recess 19 of the test probe 16 is internally threaded to be threaded onto the externally threaded adapter 23.

The handle assembly 21 also has an externally threaded adapter 24 fixed at the opposite upper end of the shaft 22 that threadably receives a knob 25 that serves as a gripping surface for manual lifting of the handle assembly 23.

The means 18 for supporting the test probe 16 on the tripod arrangement 11 also includes a guide tube 26 for example of 24 inch length and 2 inch outside diameter, and a gimbals mechanism 27 that is mounted in the tripod plate 12 for suspending the guide tube 26 along a vertical axis whether or not the tripod arrangement 11 is on a level surface or not. This gimbals mechanism 27 is constructed in a conventional manner, for example, in the form of a spherical bearing, to allow the guide tube 26 to have a universal motion within the gimbals mechanism 27.

A linear bearing 28 in the form of a bushing sleeve, for example of an anti-friction plastic material, is mounted in an upper end of the guide tube 26 in order to slidably receive the shaft 22 of the handle assembly 21 for the test probe 16. As illustrated in FIG. 1, the linear bearing 28 has a bore 29 of smaller diameter than the diameter of the handle knob 25. Consequently, the linear bearing 28 also acts as stop for the knob 25 to prevent the handle assembly 21 from sliding out of the guide tube 26.

In order to use the turf impact tester 10, the tripod leg frames 13, 14 are splayed out in order to support the tester 10 on a ground surface. At this time, the gimbals mechanism 27 insures that the guide tube 26 hangs plumb i.e. along a vertical axis to the surface between the leg frames 13, 14. Thereafter, the user by grasping the knob 25 of the handle assembly 21, lifts the test probe 16 to a predetermined height and then releases the handle assembly 21. In this respect, the length of the handle assembly 21 is prescribed such that the impact velocity of the test probe 16 against the surface is in a desired range in order to provide an appropriate impact energy. Since the handle 22 of the handle assembly 21 rides in the linear bearing 28, there is minimal friction impeding the descent of the test probe 16.

The spherical face 17 of the test probe 16 is sized to have a radius equal to that of a golf ball where the surface being tested is part of a golf course, for example a golf green. The mass of the probe in conjunction with the impact velocity is specified such that the energy of the impact is similar to that of an inbound golf ball with the target surface. For example, the radius of the face of the test probe is 0.84 inches.

The accelerometer 20 which is mounted within the test probe 16 determines the deceleration of the test probe 16 during impact with the ground surface and emits a corresponding signal in response thereto. For example, this signal is emitted to an oscilloscope (not shown) or other recording device that is operatively connected to the accelerometer 20 in order to receive the signal.

The turf impact tester 10 also includes a speed sensing means for sensing the speed of the test probe 16 prior to impact with the ground surface. By way of example, the speed sensing means includes a regular series of bands 30 (see FIG. 5) on an outer circumferential surface of the test probe 16 and a light source/light sensor (not shown) mounted on the inside of the guide tube 26 for sensing the passage of the bands 30 thereby during passage of test probe 16 through the guide tube 26. The bands 30 may be disposed in one of several different patterns, as is indicated by FIGS. 5(*a*) to 5(*f*) with greater or lesser heights. The bands 30 may be etched directly in the surface of the test probe 16 or may be printed on a label that is applied to the test probe 16, for example, adhesively.

A computer (not shown) is also operatively connected to the speed sensing means for determining the velocity of the test probe 16 prior to impact as well as to the accelerometer 20 for determining the deceleration of the test probe 16 during impact with a ground surface.

The components of the turf impact tester 10 may be made of any suitable materials. Typically, the materials would be selected to be corrosion resistant, particularly the exposed surfaces of the guide tube 26 and tripod arrangement 11. The test probe 16 is typically made of a stainless steal and has a mass in conjunction with the impact velocity as determined by the drop of the test probe 16 to be similar to that of an inbound golf ball with a target surface. Typically, the drop of the test probe is twenty (20) inches.

In this respect, the linear bearing 28 may act as a stop to limit the upward movement of the handle assembly 21 due to the abutment of the test probe 16 against the lower end of the linear bearing 28 alternatively, a mark may be placed on the handle 22 of the handle assembly 21 closer to the lower end so as to indicate the height from which the test probe 16 is to be dropped when the handle 22 is exposed.

Modeling Ball Impact

Knowing the mass of the probe permits the force between the probe and the sports field surface to be calculated via:

$$F = m_p a_p$$

where $m_p$ is the mass of the probe and
$a_p$ is the acceleration during the impact.

The velocity and displacement of the probe can be calculated via:

$$V_p = \int a_p dt + V_p^0$$

and $$d_p = \int V_p dt$$

where $V_p$ and $d_p$, are the velocity and displacement of the probe and
$V_p^0$ is the initial (pre-impact) velocity.

Figure 3:
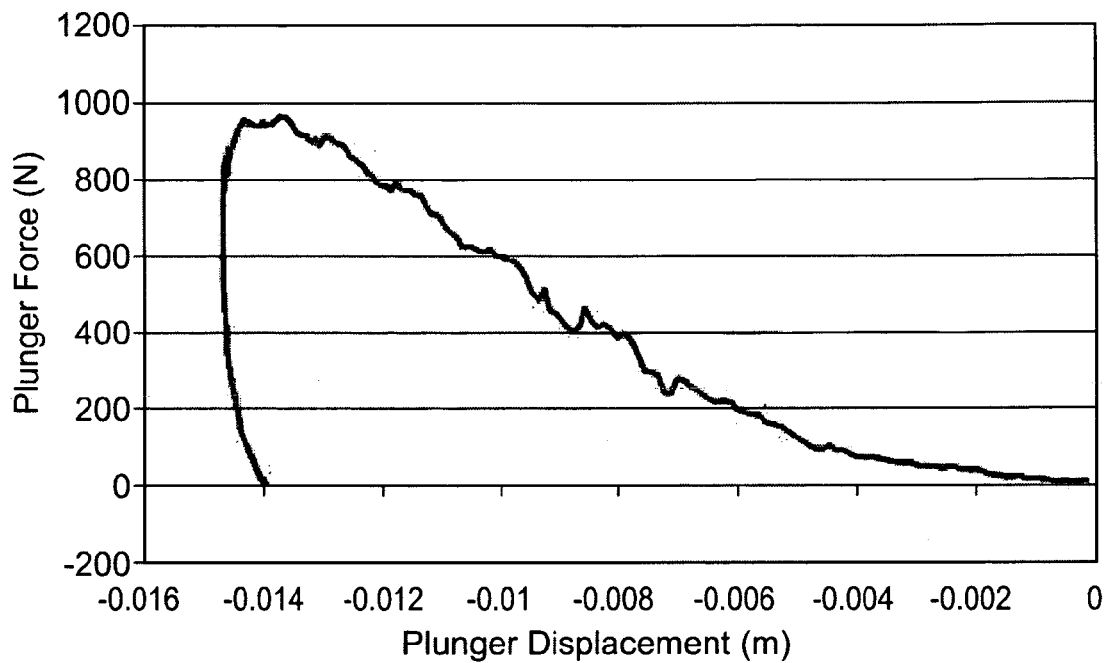
FIG. 3 illustrates a graphical representation of the impact force of the test probe (plunger) relative to the displacement of the test probe (plunger) into the ground surface.

As is usual in characterizing the response of a material to deformation, the force may be plotted as a function of displacement of the plunger. A typical result is shown in FIG. 3.

Contact as described by Hertz provides a relationship between force and displacement for elastic (reversible) materials (Johnson, K.L., "Contact Mechanics", Cambridge University Press, 1985):

$$F = \frac{4}{3} R^{\frac{1}{2}} E^* d_p^{\frac{3}{2}}$$

where R is the radius of the surface 17 of the test probe 16 and
$E^*$ is the equivalent elastic modulus of the field surface.

For contact that is dominated by permanent deformation, the force-displacement relationship may be expressed as (Johnson, 1985):

$$F = \pi a^2 P_d$$

where a is the radius of the contact area and
$P_d$ is referred to as the dynamic flow pressure of the material.

Depending on the nature of the material, the radius of contact may be expressed as a function of the displacement via (Matthews, 1980):

$$a^2 = d_p R \left[ \frac{2n+1}{2n} \right]^{2(n-1)}$$

where n denotes the strain hardening response of the material.

An elastic material is described by n=1 and a perfectly plastic material is described by n=∞. Regardless of the nature of the material, which in the case of sports fields may vary from surface type to surface type or even different areas of the same field, the contact area can be related to the displacement via:

$$a^2 = d_p K R$$

where K is a property of the surface material.

Therefore, the force and displacement can be related, for impacts with large permanent (or quasi-permanent) deformation via:

$$F = \pi K R P_d d_p$$

Both the reversible and permanent deformation relationships between force and displacement are used to fully describe the material response of the sports field surface. Referring to FIG. 4, an iterative procedure is begun to determine these material parameters. This procedure is as follows:

1) Define $d_p^{e/p}$ which defines the displacement where elastic response ends and permanent deformation begins. The selection of this displacement is arbitrary as it will be improved with future iterations, 2) From 0 to $d_p^{e/p}$, determine by minimizing the error, in a least squares sense, between the experimental data and the equation:

$$F = \frac{4}{3} R^{\frac{1}{2}} E^* d_p^{\frac{3}{2}}$$

3) From $d_p^{e/p}$ to the maximum displacement, determine $Kp_d$ by minimizing the error, in a least squares sense, between the experimental data and the equation:

$$F = \pi K R p_d (d_p - d_p')$$

where $d_p'$ is the x-axis intercept of the linear fit of the data.

4) Adjust $d_p^{e/p}$ and perform steps (2) and (3) until the error between the experimental data and the two equations for force-displacement is minimized, in a least squares sense, over the entire loading phase.

The above iterative procedure will determine the following material parameters:

Equivalent elastic modulus, $E^*$
Elastic displacement limit, $d_p^{e/p}$
Equivalent dynamic flow pressure, $p_d$ The final parameter is the dynamic yield strength. This may be calculated from (Johnson, 1985):

$$Y_d = \left[ \frac{eE^{*\frac{1}{2}} \left(\frac{1}{2} m_p V^2\right)^{\frac{1}{8}}}{3.8 R^{\frac{3}{8}}} \right]^{\frac{8}{5}}$$

where e is the coefficient of restitution of the impact.

The invention thus provides a technique for determining the relative impact properties of a sports field surface in a simple reliable manner as well as a relatively simple and reliable structure for measuring the impact properties of a sports field surface.

The invention further provides a turf tester that is easy to carry and set up and one that can be readily moved from place to place to take several readings over an extended area in a minimum of time. This facilitates use by groundskeepers to maintain a level of consistency in the hardness characteristics of the golf greens of a golf course or any other sports field being maintained.

The turf tester may also be used to obtain information from the material parameters derived in the analysis of obtained experimental data to predict the resulting bounce of a sports ball on the sports field surface of interest.

What is claimed is:

1. A turf impact tester comprising
a support;
a test probe having a part-spherical impact surface;
means for supporting said test probe in said support for movement under gravity along a vertical axis from a predetermined position to a position of impact with a ground surface; and
an accelerometer for determining the deceleration of said test probe during impact with the ground surface and emitting a corresponding signal in response thereto.

2. A turf impact tester as set forth in claim 1 further comprising a speed sensing means for sensing the speed of said test probe prior to impact with a ground surface.

3. A turf impact tester as set forth in claim 2 wherein said speed sensing means includes a regular series of bands on an outer circumferential surface of said test probe for sensing thereof at a predetermined point of said guide tube during passage of said test probe through said guide tube.

4. A turf impact tester as set forth in claim 1 wherein said support is a tripod arrangement and said means for supporting said test probe is mounted on said tripod arrangement to suspend said test probe along said vertical axis.

5. A turf impact tester as set forth in claim 4 wherein said means for supporting said test probe includes a guide tube slidably receiving said test probe and a gimbals mechanism mounted on said tripod arrangement and receiving said guide tube therein for suspending said guide tube along said vertical axis.

6. A turf impact tester as set forth in claim 5 wherein said means for supporting said test probe further includes a handle slidably mounted in said guide tube and receiving said test probe at a lower end and a knob at an upper end of said handle for abutting said guide tube.

7. A turf impact tester as set forth in claim 1 wherein said accelerometer is mounted in said test probe.

8. A turf impact tester comprising
a tripod arrangement;
a gimbals mechanism mounted on said tripod arrangement;
a guide tube mounted in said gimbals mechanism for suspension from said tripod arrangement along a vertical axis;
a linear bearing mounted in an upper end of said guide tube and disposed on said vertical axis;
a handle slidably mounted in said bearing for movement along said vertical axis;
a test probe secured to a lower end of said handle and having a surface for impacting a ground surface;
a knob mounted on an upper end of said handle for abutting said guide tube; and
an accelerometer for measuring the deceleration of said test probe in response to an impact with a ground surface.

9. A turf impact tester as set forth in claim 8 further comprising a speed sensing means for sensing the speed of said test probe prior to impact with a ground surface.

10. A turf impact tester as set forth in claim 8 wherein said test probe has a part spherical surface for impacting against a ground surface.

11. A turf impact tester as set forth in claim 10 wherein said surface of said test probe has a radius equal to a radius of a golf ball.

12. A turf impact tester as set forth in claim 10 wherein said test probe has a predetermined mass.

13. In a method of testing a sports field surface, the steps of
positioning a test probe having a part-spherical impact surface at a predetermined position above a ground surface;
dropping the test probe under gravity from said predetermined position to impact with the ground surface;
determining the deceleration of the test probe during impact with the ground surface and emitting a corresponding signal in response thereto; and
plotting the force of the test probe on the ground surface as a function of the displacement of the test probe into the ground surface.

14. A method as set forth in claim 13 further comprising the step of calculating the equivalent elastic modulus ($E^*$) of the ground surface using the relationship $$F = \frac{4}{3} R^{\frac{1}{2}} E^* d_p^{\frac{3}{2}}$$

where F is the force between the test probe and the ground surface,
R is the radius of the impact surface of the test probe and
$d_p$ is the displacement of the test probe.

15. A method as set forth in claim 14 further comprising the steps of calculating the dynamic yield strength of the ground surface from the relationship $$Y_d = \left[ \frac{eE^{*\frac{1}{2}} \left(\frac{1}{2} m_p V^2\right)^{\frac{1}{8}}}{3.8 R^{\frac{3}{8}}} \right]^{\frac{8}{5}}$$

where e is the coefficient of restitution of the impact.

* * * * *

UNITED STATES PATENT AND TRADEMARK OFFICE
CERTIFICATE OF CORRECTION

| | |
|---|---|
| PATENT NO. | : 7,243,526 B2 |
| APPLICATION NO. | : 11/060107 |
| DATED | : July 17, 2007 |
| INVENTOR(S) | : Pringle et al. |

It is certified that error appears in the above-identified patent and that said Letters Patent is hereby corrected as shown below:

Col. 10, line 9-14; Please insert;

16. A method as set forth in claim 14 wherein the mass of said test probe and the impact force F with the ground surface are predetermined whereby the energy of impact is similar to that of an inbound ball with said ground surface.

17. A method as set forth in claim 13 wherein said surface of said test probe has a radius equal to a radius of a golf ball.

Signed and Sealed this

Sixteenth Day of October, 2007

JON W. DUDAS
*Director of the United States Patent and Trademark Office*